(12) United States Patent
Tsoupas et al.

(10) Patent No.: US 8,063,381 B2
(45) Date of Patent: Nov. 22, 2011

(54) ACHROMATIC AND UNCOUPLED MEDICAL GANTRY

(75) Inventors: Nicholaos Tsoupas, Center Moriches, NY (US); Dmitry Kayran, Rocky Point, NY (US); Vladimir Litvinenko, Mt. Sinai, NY (US); William W. MacKay, Wading River, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 306 days.

(21) Appl. No.: 12/403,486

(22) Filed: Mar. 13, 2009

(65) Prior Publication Data

US 2010/0230620 A1    Sep. 16, 2010

(51) Int. Cl.
*H01J 29/02* (2006.01)

(52) U.S. Cl. ......... 250/396 ML; 250/492.1; 250/492.3; 250/505.1; 250/396 R; 315/500; 315/501; 315/503

(58) Field of Classification Search ......... None
See application file for complete search history.

(56) References Cited

U.S. PATENT DOCUMENTS

| | | | |
|---|---|---|---|
| 4,870,287 A | 9/1989 | Cole et al. | |
| 5,198,674 A * | 3/1993 | Underwood | 250/396 ML |
| 6,476,403 B1 | 11/2002 | Dolinskii et al. | |
| 6,693,283 B2 | 2/2004 | Eickhoff et al. | |
| 0,262,269 A1 | 11/2007 | Trbojevic et al. | |
| 2003/0164458 A1* | 9/2003 | Eickhoff et al. | 250/491.1 |
| 2004/0113099 A1* | 6/2004 | Eickhoff et al. | 250/492.3 |
| 2007/0029510 A1* | 2/2007 | Hermann et al. | 250/493.1 |
| 2007/0170994 A1* | 7/2007 | Peggs et al. | 331/34 |
| 2007/0262269 A1* | 11/2007 | Trbojevic | 250/492.3 |

OTHER PUBLICATIONS

Amaldi, U., et al., "Recent applications of Synchrotrons in cancer therapy with Carbon Ions", europhysics news, pp. 114-118 (2005).
Benedikt, M., et al., "Matching to gantries for medical synchrotrons", Particle Accelerator Conference PAC '97, pp. 1379-1381 (1997).
Meyers, F., "A Heavy Ion Accelerator Gears Up to Fight Cancer", Science, vol. 261 (5126), p. 1270 (1993).
Normile, D., "Heavy Ions Pack Powerful Punch", Science, vol. 278 (5345), p. 1884 (1997).
'Siemens Particle Therapy Technology'. Siemens Healthcare. [online] [retrieved on Apr. 21, 2008]. Retrieved from the Internet: http://www.medical.siemens.com/webapp/wcs/stores/servlet/CategoryDisplay~q_catalogId~e_-1~a_categoryId~e_1009405~a_catTree~e_100010,1008643,1009404,1009405~a_langId~e_-1~a_storeId~e_10001.htm.
'Heavy Ion Cancer Therapy: 48 StarCell 300-order for Varian'. Varian's High Energy Physics Solutions Newsletter [online]. Mar. 2005, edition I. Retrieved from the Internet: www.varianinc.com/image/vimage/docs/products/vacuum/news/shared/Solutions_03_05.pdf.

* cited by examiner

*Primary Examiner* — Robert Kim
*Assistant Examiner* — Michael Logie
(74) *Attorney, Agent, or Firm* — Dorene M. Price

(57) ABSTRACT

A medical gantry that focus the beam from the beginning of the gantry to the exit of the gantry independent of the rotation angle of the gantry by keeping the beam achromatic and uncoupled, thus, avoiding the use of collimators or rotators, or additional equipment to control the beam divergence, which may cause beam intensity loss or additional time in irradiation of the patient, or disadvantageously increase the overall gantry size inapplicable for the use in the medical treatment facility.

27 Claims, 11 Drawing Sheets

ACHROMATIC AND UNCOUPLED MEDICAL GANTRY

This invention was made with Government support under contract number DE-AC02-98CH10886, awarded by the U.S. Department of Energy. The Government has certain rights in the invention.

BACKGROUND OF THE INVENTION

I. Field of the Invention

This invention relates generally to a cancer therapy and, more particularly, to a medical particle delivery system having an achromatic and uncoupled gantry design.

II. Background of the Related Art

In traditional radiation therapy, X-ray beams are typically used to treat cancer. However, X-rays release much of their energy quickly after penetrating the skin, disrupting the molecules of healthy tissue and organs. Protons, neutron, $\alpha$-ray or other ion rays, on the other hand, have excellent physical properties for radiation therapy which permit one to control very precisely the shape of the dose distribution inside the patient's body. The dose delivered by such an ion ray beam is well localized in space, not only in the lateral direction, but also very precisely in depth, due to the presence of the characteristic Bragg peak. Thus, ion ray therapy is effective because of its ability to accurately target and kill tumors, both near the surface and deep seated within the body, while minimizing damage to the surrounding tissues. For this reason, it is favored for treating certain kinds of tumors where conventional X-ray and radiation oncology would damage surrounding tissues to an unacceptable level.

It has been known in the art to use a particle accelerator, such as a synchrotron, and a gantry arrangement to deliver a beam of ion particles from a single source to one of a plurality of patient treatment stations for cancer therapy. Such cancer treatment facilities are widely known throughout the world. For example, U.S. Pat. No. 4,870,287 to Cole et al. discloses a multi-station proton beam therapy system for selectively generating and transporting proton beams from a single proton source and accelerator to one of a plurality of patient treatment stations each having a rotatable gantry for delivering the proton beams at different angles to the patients.

The beam delivery portion of the Cole et al. system includes a switchyard and gantry arrangement. The switchyard utilizes switching magnets that selectively direct the proton beam to the desired patient treatment station. Each patient treatment station includes a gantry having an arrangement of three bending dipole magnets and two focusing quadrupole magnets between each set of bending dipole magnets. The gantry is fully rotatable about a given axis so that the proton beam may be delivered at any desired angle to the patient located at the isocenter of the gantry. The gantry of typical particle beam cancer therapy systems accepts a particle beam of a required energy from the accelerator and projects it with a high precision toward a cancerous tumor within a patient. The beam from the gantry must be angularly adjustable so that the beam can be directed into the patient from above and all sides.

The disadvantage of such a gantry arrangement, however, that if the non-symmetric ion beam (i.e., a beam having different emittances in vertical and horizontal planes) is introduced into the gantry from a fixed transfer line, the beam transport within the gantry arrangement of Cole et al. becomes dependent on the angle of gantry rotation, which means that the patient will not receive the same high-precision beam spot from every direction.

In order to circumvent the disadvantage of the Cole et al. system, it has been proposed to include within a gantry setup a collimator, a special device that narrows a beam by filtering the beam particles so that only the rays traveling parallel to a specified direction are allowed through. Naturally the drawback of using such a device is a significant beam intensity loss and/or continuous beam tuning, which may require additional unnecessary time during the irradiation of the patient.

Benedikt, et al., on the other hand, proposed to use a special matching section, called a "rotator," which in essence a plurality of quadrupole magnets positioned just in front of the gantry present in addition to the quadrupole magnets within the gantry. (M. Benedikt and C. Carli, "Matching to gantries for medical synchrotrons", *Particle Accelerator Conference PAC '97*, Vancouver 1997). The rotator allows for the section of the beam line just before the gantry to be synchronously rotated in proportion to the gantry rotation. However, the disadvantage of the Benedikt et al. system is that it occupies about 10 m of extra length of the transfer line and requires an extra equipment for extremely precise mechanical rotation, which is a significant drawback for design of compact medical accelerator complexes appropriate for use in the hospital facilities.

Yet another approach to overcome beam dependence on the angle of gantry rotation was proposed by Dolinskii and disclosed in the U.S. Pat. No. 6,476,403. The gantry design of Dolinskii is based on a plurality of quadrupoles that create a fully achromatic beam transport, which is independent of gantry rotation. Nonetheless, the drawback of such a system is that the beam at the entrance of the gantry must be constrained to have the same angular divergence or size in the horizontal and vertical planes, which requires additional system to control the beam itself.

Accordingly, it would be desirable to focus the beam in such a way that the focusing of the beam at the exit of the gantry is always independent of the rotation angle of the gantry, thus, avoiding the use of collimators, rotators, or additional equipment to control the beam divergence, which may cause beam intensity loss or additional time in irradiation of the patient, or disadvantageously increase the overall gantry size inapplicable for the use in the medical treatment facility.

SUMMARY OF THE INVENTION

In view of the above-described problems and goals, the present invention provides for a particle therapy gantry for delivering a particle beam to a patient independent of the gantry rotation by maintaining the particle beam achromatic and linearly uncoupled.

The medical gantry includes a plurality of dipole magnets that bend the trajectory of the beam path onto a patient, and a plurality of quadrupole magnets that focus the beam and maintain a small, high-precision beam spot at the patient by creating an achromatic and linearly uncoupled conditions at the exit of the gantry independent of its rotation.

In one embodiment, the beam tube of the gantry preferably includes a particle beam entry point, a transition path, a particle beam exit point, a first dipole sector bend of the particle beam path, a second dipole sector bend of the particle beam path, and a third dipole sector bend of the particle beam path. In one embodiment, the first and the second dipole sector bends of the particle beam path provide a parallel translation of the beam in the plane if the bend are equal but opposite. In an alternative embodiment, the first and the second dipole sector bend of the particle beam path do not provide a parallel translation of the beam in the plane as exemplified below. The third sector bend of the particle beam path directs the particle beam to the isocenter of the gantry, in the direction of a patient. The particle beam passing through each sectors may be bend by any desired angle as long as the combinations of three bends redirects the particle beam to the isocenter of the beam path. In one embodiment, the combination of three angles, by which the beam path is bend, is about ninety degrees.

In further embodiment, the beam tube of the gantry preferably includes a plurality of quadrupole magnets to control the beam size and shape at the exit of the gantry to afford the rotation of the gantry independent of the beam. In one embodiment, the gantry includes six quadrupole magnets positioned between the first and the second dipole sector bends and six quadrupole magnets positioned between the second and the third dipole sector bends arranged in symmetrical pairs about the center between the sector bends to produce achromatic and uncoupled beam transfer.

In another embodiment, the gantry includes in additional to the symmetrically positioned six quadrupole magnets between dipole sector bends, a quadrupole magnet positioned at the line center between the first and the second dipole sector bends and/or between the second and the third dipole sector bends to produce achromatic and uncoupled beam transfer with additional control on the β functions to reduce the aperture of the second and/or third dipole.

In yet another embodiment, the gantry includes eight quadrupole magnets, where four are positioned along the axis of rotation before the first dipole sector bend, two are positioned between the first and the second dipole sector bends and two are positioned between the second and the third dipole sector bends arranged to produce achromatic and uncoupled beam transfer.

In one embodiment, the size and shape of the particle beam at the exit of the gantry is independent of the angle of gantry rotation, and wherein the gantry can be rotated by any angle between 0 and 360 with respect to a fixed incoming beam line.

In further embodiment each pair of quadrupoles is excited at the same strength to achieve the achromatic conditions and to satisfy the condition $R_x=R_y$. The strength and the location of the plurality of quadrupoles is determined by the achromaticity condition $R_{16}=0$ and $R_{26}=0$, the mirror symmetry of the particle beam, which requires that $R_{11}=R_{22}$ and $R_{33}=R_{44}$ and the decoupling condition Rx=Ry.

In further embodiment, the strength and the location of the plurality of quadrupoles are maintained to achieve the β functions of less than about 30 m between a set of dipoles and the β functions of less than about 5.5 m at the exit of the third dipole. The drift between the first and the second dipole magnet is about 5 m.

The present invention further involves a method for delivering a particle beam to a patient through a gantry. The method generally includes the steps of bending the particle beam with a plurality of fixed field dipole magnets sequentially arranged along a beam path of the gantry, and the steps of maintaining achromatic and uncoupled conditions of the beam at the exit of the gantry with a plurality of quadrupole magnets which are arranged symmetrically in pair between the fixed field dipole magnets. The method additionally includes the steps of providing β function control by incorporating an additional quadrupole magnet at the center between the two dipole sector bends.

The gantry of the present invention may be utilized in a medical particle beam therapy system having a source of particles, a particle accelerator, an injector for transporting particles from the source to the accelerator, one or more patient treatment stations including rotatable gantries of the present invention for delivering a particle beam to a patient and a beam transport system for transporting the accelerated beam from the accelerator to the patient treatment station.

The preferred embodiments of the particle beam gantry of the present invention, as well as other objects, features and advantages of this invention, will be apparent from the following detailed description, which is to be read in conjunction with the accompanying drawings. The scope of the invention will be pointed out in the claims.

DETAILED DESCRIPTION OF THE INVENTION

The above and other objectives of the invention will become more apparent from the following description and illustrative embodiments which are described in detail with reference to the accompanying drawings. Similar elements in each figure are designated by like reference numbers and, hence, subsequent detailed descriptions thereof may be omitted for brevity.

Figure 1:
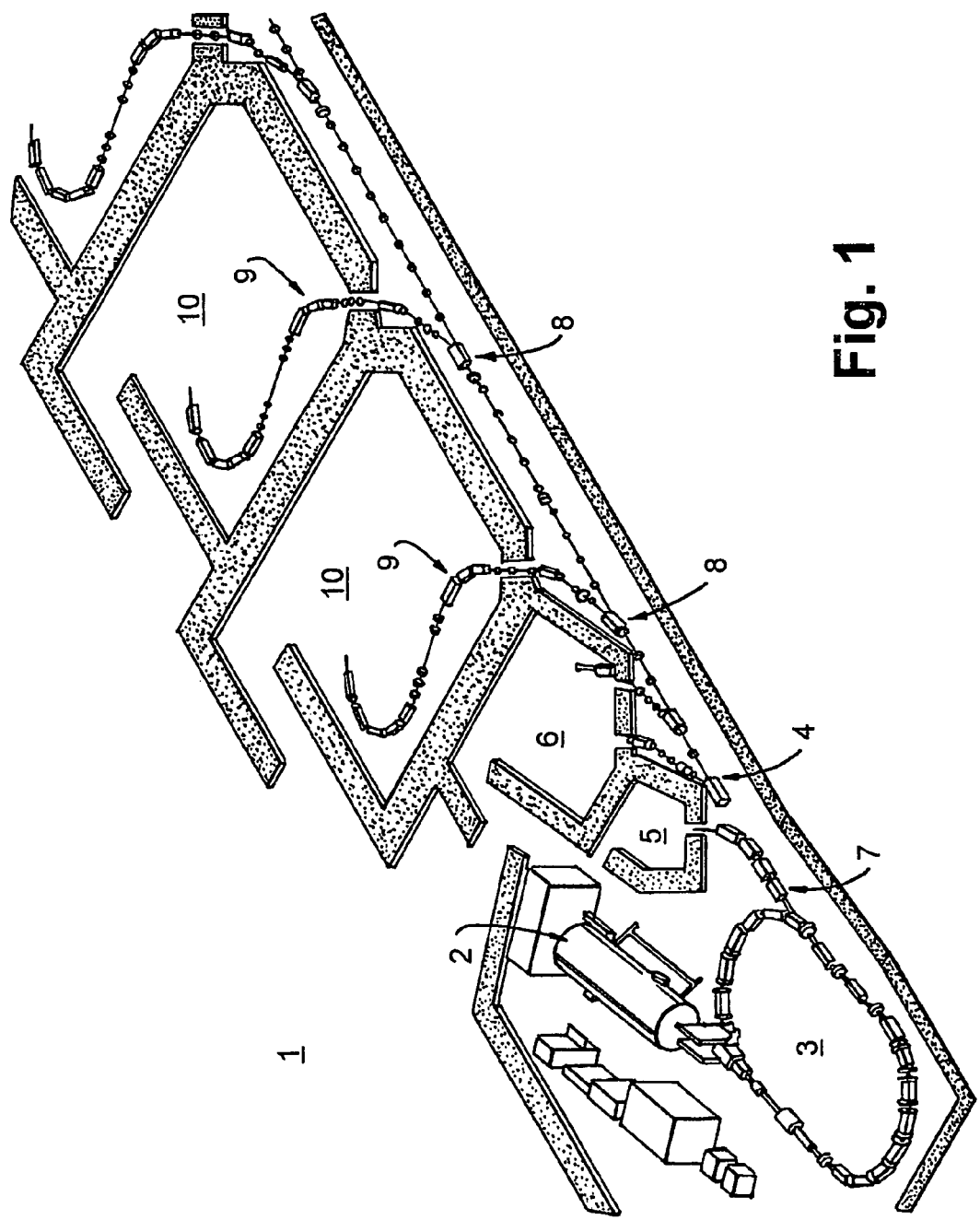
FIG. 1 is a top plan view of a typical medical particle delivery therapy facility.

FIG. 1 shows a typical medical particle delivery therapy facility 1. The facility 1 generally includes an injector 2, a particle accelerator 3, and a beam delivery network 4 including a rotatable gantry treatment room 10 for delivering a beam to a patient. The beam delivery network 4 may also be designed to divert independent beams to various other applications as desired. For example, the beam delivery network 4 may be designed to deliver a beam to a beam research room 5 and a fixed beam treatment room 6. The research room 5 may be provided for research and calibration purposes, with an entrance separate from the patient areas, while the fixed beam treatment room 6 may include separate beam lines for such therapeutic applications, such as eye treatments.

The beam injector module 2 can be a conventional LINAC or a tandem Van de Graaf injector with an injection kicker, which completes the task of particle injection into the accelerator 3. In the case of proton particles, the injector typically provides proton beam pulses at 30 Hz with a pulse width varying between 25 and 100 nanoseconds at a delivered energy of 7 MeV.

The particle accelerator 3 can be a synchrotron, cyclotron or some other conventional design known in the prior art. The accelerator 3 accelerates particles to a desired energy level for extraction and delivery to the patient treatment rooms 6 and 10. Variation of the extraction energy is achieved by adjusting, for example, an RF frequency within the accelerator 3. Again for proton particles, extraction typically occurs when the kinetic energy of the particles is in the range 60 to 250 MeV. For examples, see U.S. Pat. No. 4,870,287 to Cole et al. incorporated herein in its entirety by reference.

The beam delivery network 4 connects the accelerator 3 to the treatment rooms 6 and 10 and the beam research room 5. The network 4 generally includes an extraction line 7, a switchyard 8 and a plurality of beam transport lines 9. The switchyard 8 is typically an arrangement of switching magnets for diverting the particle beam to a desired beam line 9. The beam transport lines 9 take the particle beam from the switchyard 8 to the different treatment rooms of the facility 6 and 10.

Figure 2:
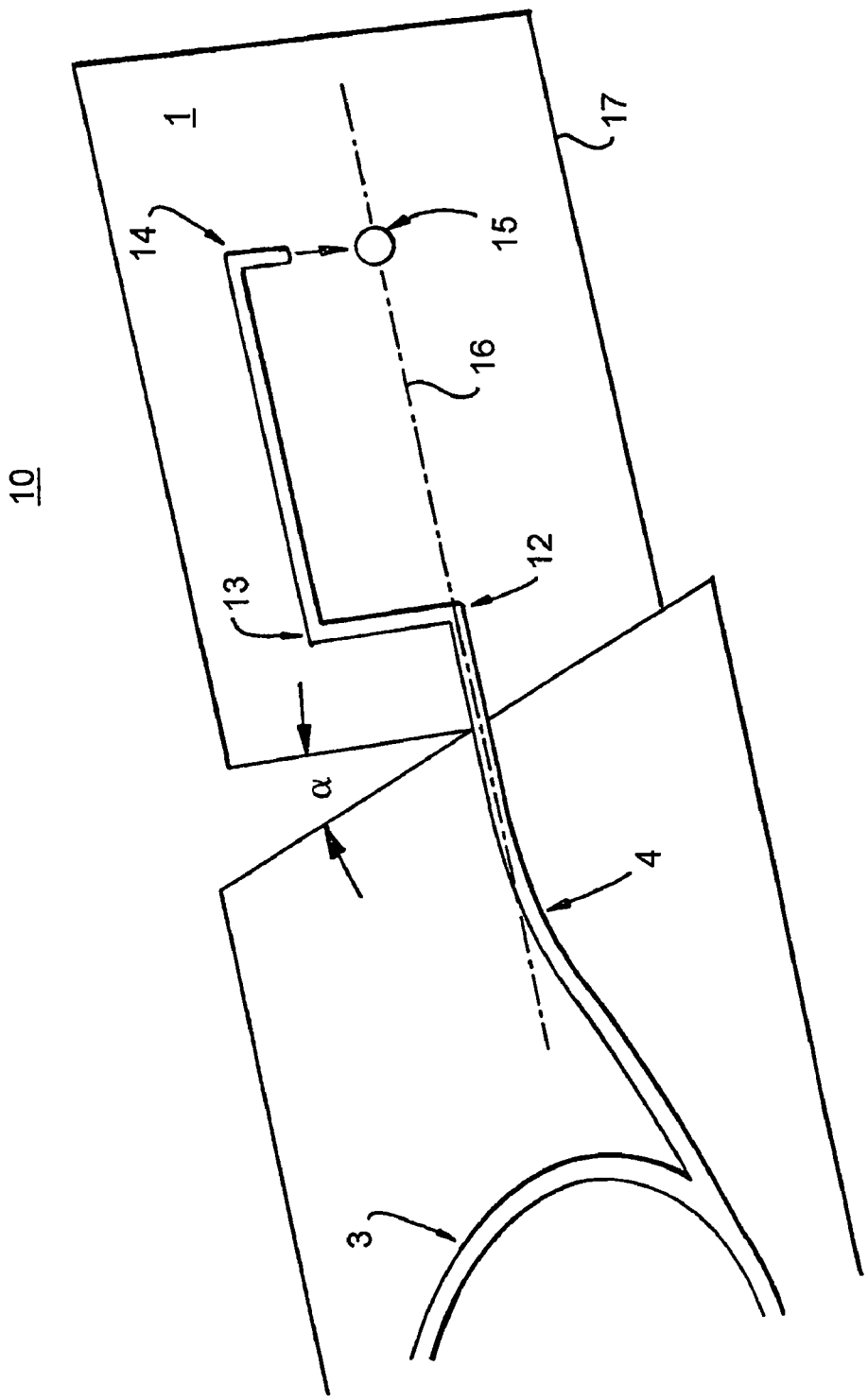
FIG. 2 is a schematic view of a rotating gantry.

FIG. 2 shows schematic representation of the rotatable gantry treatment room 10 includes a rotating gantry 11, which is rotatable by plus or minus 200 degrees from the vertical about an axis of rotation 16 to deliver a particle beam to a patient at a gantry isocenter 15. The gantry system accepts particles already accelerated to required energy delivered by the beam delivery network 4 from the particle accelerator 3. The first part 12 of the gantry bends particles by a certain angle normally less than 90°. The second part 13 of the gantry bends the particles by same or similar angle of the first part 12 but in the opposite direction. The third part 14 of the gantry bends the particle by approximately 90° but may be different as long as the bending of the beam by three dipole magnets 12, 13 and 14 brings the particles towards the required direction of the isocenter 15.

The gantry 11 is constructed as a three-dimensional structure supported by multiple bearings on the treatment room side and, on the beam inlet side. The gantry is further preferably balanced around its rotation axis. Gantry movement can be realized by a gear motor/gear ring drive that allows high precision positioning. Each gantry is preferably controlled by means of an individual independent computer unit that ensures mutual braking of the main drive units, soft start and soft deceleration functions, control of the auxiliary drive units for the treatment room, and supervision of the limit switches. The gantry further includes a nozzle for delivering the particle beam to the patient and may further include a plurality of scanning magnets. For examples, see U.S. Pat. No. 4,870,287 to Cole et al. and U.S. Pat. App. No. 2007/0262269 to Trbojevic et al., all incorporated herein in their entirety by reference.

The beam generated by the particle accelerator normally is non-symmetric and have different emittances in horizontal and vertical planes. The non-symmetry of the beam complicates the matching of the transfer line to the rotating gantry. The input beam parameters in the horizontal and vertical planes of the gantry become a function of the angle of gantry rotation and are transformed to the beam parameters at the gantry exit. However the matching of the transfer line to the rotating gantry for the non-symmetrical beam independent of the gantry angle of rotation can be made. This is explained below, by using a beam line which displaces the beam in both the horizontal and vertical planes simultaneously, with the beam line preserving achromatic and linearly uncoupled conditions of beam transfer.

Matrix Analysis

The beam can be mathematically described by a 6×6 σ-matrix that have form:

$$\sigma-\text{matrix} = \begin{pmatrix} \sigma_{11} & \sigma_{12} & \sigma_{13} & \sigma_{14} & \sigma_{15} & \sigma_{16} \\ \sigma_{21} & \sigma_{22} & \sigma_{23} & \sigma_{24} & \sigma_{25} & \sigma_{26} \\ \sigma_{31} & \sigma_{32} & \sigma_{33} & \sigma_{34} & \sigma_{35} & \sigma_{36} \\ \sigma_{41} & \sigma_{42} & \sigma_{43} & \sigma_{44} & \sigma_{45} & \sigma_{46} \\ \sigma_{51} & \sigma_{52} & \sigma_{53} & \sigma_{54} & \sigma_{55} & \sigma_{56} \\ \sigma_{61} & \sigma_{62} & \sigma_{63} & \sigma_{64} & \sigma_{65} & \sigma_{66} \end{pmatrix} \quad (1)$$

where the matrix describes a beam which is distributed in Gaussian space in any of the six coordinates (x, x', y, y', δ1, δp/p$_0$). The size or the angular divergence of the beam is given by the square root of the diagonal terms of the σ-matrix. If the beam is uncoupled and achromatic, the elements of the σ-matrix coupling in the horizontal and vertical phase vanish and the σ-matrix can be expressed as:

$$\sigma-\text{matrix} = \begin{pmatrix} \sigma_{11} & \sigma_{12} & 0 & 0 & 0 & 0 \\ \sigma_{21} & \sigma_{22} & 0 & 0 & 0 & 0 \\ 0 & 0 & \sigma_{33} & \sigma_{34} & 0 & 0 \\ 0 & 0 & \sigma_{43} & \sigma_{44} & 0 & 0 \\ 0 & 0 & 0 & 0 & \sigma_{55} & 0 \\ 0 & 0 & 0 & 0 & 0 & \sigma_{66} \end{pmatrix} \quad (2)$$

Such conditions are expected for the σ-matrix at the entrance ($\sigma_{entr}$) of the gantry. However, if the gantry is rotated with respect to the incoming beam by an angle α, the σ-matrix of the beam at the gantry exit is given by the transformation:

$$\sigma_{exit}(\alpha) = R(\alpha) \cdot \sigma_{ent} \cdot R(\alpha)^T \quad (3)$$

where $R(\alpha)^T$ is a transpose matrix of $R(\alpha)$, which represents a beam transport system (an arrangement of quadrupole and dipole magnets) that allow to transport the beam (σ-matrix) from the entrance ($\sigma_{entr}$) to the exit ($\sigma_{exit}$) of the gantry at a defined rotation of the gantry α. Mathematically $R(\alpha)$ can be expressed as:

$$R(\alpha) = R_{rot}(\alpha) \cdot R_{trans} \cdot R_{rot}(\alpha)^T \quad (4)$$

where $R(\alpha)$ is the product of the gantry rotation matrix ($R_{rot}(\alpha)$) and the transfer matrix ($R_{trans}$). The rotation matrix $R_{rot}(\alpha)$ describes the rotation of the coordinate system by an angle α represented by $$R_{rot}(\alpha) = \begin{matrix} \cos(\alpha) & 0 & \sin(\alpha) & 0 \\ 0 & \cos(\alpha) & 0 & \sin(\alpha) \\ -\sin(\alpha) & 0 & \cos(\alpha) & 0 \\ 0 & -\sin(\alpha) & 0 & \cos(\alpha) \end{matrix} \quad (5)$$

and the transfer matrix $R_{trans}$ describes quadrupole arrangements within gantry represented by $$R_{trans} = \begin{pmatrix} R_{11} & R_{12} & R_{13} & R_{14} & R_{15} & R_{16} \\ R_{21} & R_{22} & R_{23} & R_{24} & R_{25} & R_{26} \\ R_{31} & R_{32} & R_{33} & R_{34} & R_{35} & R_{36} \\ R_{41} & R_{42} & R_{43} & R_{44} & R_{45} & R_{46} \\ R_{51} & R_{52} & R_{53} & R_{54} & R_{55} & R_{56} \\ R_{61} & R_{62} & R_{63} & R_{64} & R_{65} & R_{66} \end{pmatrix} \quad (6)$$

In order for the beam transport system to keep the beam uncoupled and achromatic, the $R(\alpha)$ matrix must be expressed as $$R_{trans} = \begin{pmatrix} R_{11} & R_{12} & 0 & 0 & 0 & 0 \\ R_{21} & R_{22} & 0 & 0 & 0 & 0 \\ 0 & 0 & R_{33} & R_{34} & 0 & 0 \\ 0 & 0 & R_{43} & R_{44} & 0 & 0 \\ 0 & 0 & 0 & 0 & 1 & 0 \\ 0 & 0 & 0 & 0 & 0 & 1 \end{pmatrix} \quad (7)$$

By solving the product matrix, i.e., eq. 3, for beam shape at the exit of the gantry ($\sigma_{exit}$), the beam becomes dependent on the angle of gantry rotation. However, in order for the beam transport system to be independent of the rotation angle, the non-zero matrix elements $R_{ij}$ of the $R_{trans}$ matrix must be constant and have a form:

$$R_{trans} = \begin{pmatrix} R_{11} & R_{12} & 0 & 0 & 0 & 0 \\ R_{21} & R_{22} & 0 & 0 & 0 & 0 \\ 0 & 0 & R_{11} & R_{12} & 0 & 0 \\ 0 & 0 & R_{21} & R_{22} & 0 & 0 \\ 0 & 0 & 0 & 0 & 1 & 0 \\ 0 & 0 & 0 & 0 & 0 & 1 \end{pmatrix} \quad (8)$$

where $R_{11}=R_{33}$, $R_{21}=R_{43}$, $R_{12}=R_{34}$, and $R_{22}=R_{44}$ or $R_{11}=R_{33}=R_{21}=R_{43}=R_{12}=R_{34}=R_{22}=R_{44}=0$ if the gantry system does not employ skew quadrupole magnets. Without restraining the incoming beam represented by $\sigma_{entr}$, it is feasible to eliminate any dependence of the beam on the gantry rotation as long as the matrix elements of the gantry's R matrix satisfy the conditions appearing in eq. (8).

Achromatic Conditions

Dispersion in the particle beam refers to a phenomenon of particle deviation from the original trajectory due the fact that the particle beam comprises an ensemble of many particles with different momenta. Dispersion is created by beam transport elements such as dipole magnets that bend the reference trajectory of the beam, whereas typical dispersion-free elements are drift space and quadrupole magnets. Without special precautions, a beam-transport system containing bending dipole magnets is, in general, chromatic.

However, to realize the achromatic condition, the transport matrix of the first sector dipole (1) may be written in the form of 2×2 blocks as $$B_1 = \begin{pmatrix} M_x & 0 & D \\ 0 & M_y & 0 \\ -\tilde{D} & 0 & G \end{pmatrix}, \quad (9)$$

where $$M_x = \begin{pmatrix} \cos\phi & \rho\sin\phi \\ -\frac{1}{\rho}\sin\phi & \cos\phi \end{pmatrix},$$

$$M_y = \begin{pmatrix} 1 & \rho\phi \\ 0 & 1 \end{pmatrix},$$

$$D = \begin{pmatrix} 0 & \rho(1-\cos\phi) \\ 0 & \sin\phi \end{pmatrix},$$

$$G = \begin{pmatrix} 1 & G \\ 0 & 1 \end{pmatrix}$$

$$\tilde{D} = \sigma_y D^T \sigma_y = \begin{pmatrix} -\sin\phi & -\rho(1-\cos\phi) \\ 0 & 0 \end{pmatrix},$$

with the Pauli matrix $$\sigma_y = \begin{pmatrix} 0 & -i \\ i & 0 \end{pmatrix}.$$

Figure 3:
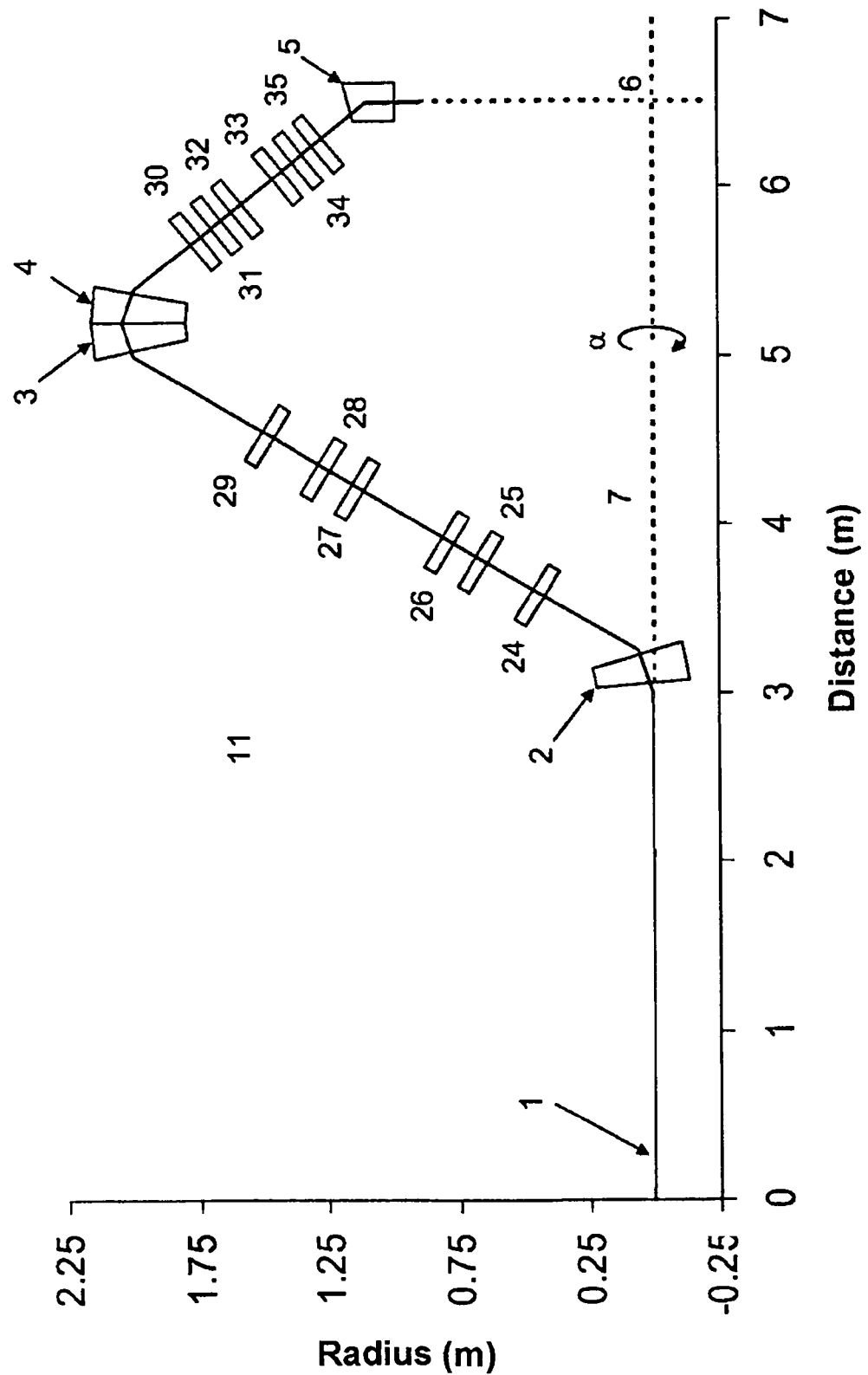
FIG. 3 is a cross-sectional view of the gantry with six (6) quadrupole magnets between each dipole pair to control beam achromaticity and coupling according to the present invention.

The angles $\phi$ and $\rho$ represent the bend angles produced by the first and second dipole magnets (see FIG. 3).

The reverse second bend has the matrix characterized by $$B_2 = \begin{pmatrix} M_x & 0 & -D \\ 0 & M_y & 0 \\ \tilde{D} & 0 & G \end{pmatrix} \quad (10)$$

with only the upper right and lower left 2×2 blocks of opposite sign from $B_1$. Both bends have the same diagonal blocks.

While the transport between the two dipoles might contain quadrupoles of various rotations about the gantry beam transfer line, it is simpler to start with a transversely decoupled solution relative to the plane of the two bends. Thus, it is desirable to find a configuration of quadrupoles and drifts which will zero the dispersion terms $R_{16}$ and $R_{26}$ of the whole section of beam:

$$R(\alpha) = B_2 M B_1 \quad (11)$$

$$= \begin{pmatrix} M_x & 0 & D \\ 0 & M_y & 0 \\ -\tilde{D} & 0 & G \end{pmatrix} \begin{pmatrix} N_x & 0 & 0 \\ 0 & N_y & 0 \\ 0 & 0 & I \end{pmatrix} \begin{pmatrix} M_x & 0 & -D \\ 0 & M_y & 0 \\ \tilde{D} & 0 & G \end{pmatrix}$$

$$= \begin{pmatrix} M_x N_x M_x & 0 & M_x N_x D - D \\ 0 & M_y N_y M_y & 0 \\ \tilde{D} N_x M_x - \tilde{D} & 0 & \tilde{D} N_x D + G^2 \end{pmatrix}$$

since $D\tilde{D}=0$, $DG=D$, and $G\tilde{D}=\tilde{D}$. In order to cancel the dispersion, $M_x N_x D$ must equal $D$, i.e., the second column of $D$ must be an eigenvector of $M_x N_x$ with eigenvalue of 1. Rearranging the achromatic condition gives the pair of equations:

$$\begin{pmatrix} a & b \\ d & c \end{pmatrix} \begin{pmatrix} -\rho(1-\cos\alpha) \\ \sin\alpha \end{pmatrix} = \begin{pmatrix} -\rho(1-\cos\alpha) \\ \sin\alpha \end{pmatrix} \quad (12)$$

with explicit elements a, b, c, and d for $N_x$. These two equations, together with requirement $\det(N_x)=1$, yield three equations in four unknowns. Eliminating three of the variables, we get $$N_x = \begin{pmatrix} a & -(1+a)\rho\tan\frac{\phi}{2} \\ \frac{1-a}{\rho}\cot\frac{\phi}{2} & a \end{pmatrix} \quad (14)$$

which has identical values on the diagonal. Given values of $\phi$ and $\rho$ for the bends are constant, then there is only one degree of freedom left in $N_x$ for $R(\alpha)$ to be achromatic, with only 2×2 blocks along the diagonal of $R(\alpha)$ and blocks of zeros away from the diagonal.

Uncoupled Conditions

Pivoting the section of gantry about the incoming beam (dashed line of FIG. 3) by an angle $\alpha$ would tend to produce xy-coupling when $\alpha$ is not a multiple of 90°:

$$R(\alpha) = \begin{pmatrix} I\cos\alpha & I\sin\alpha \\ -I\sin\alpha & I\cos\alpha \end{pmatrix} \begin{pmatrix} R_x & 0 \\ 0 & R_y \end{pmatrix} \begin{pmatrix} I\cos\alpha & -I\sin\alpha \\ I\sin\alpha & I\cos\alpha \end{pmatrix} \quad (15)$$

$$= \begin{pmatrix} R_x\cos^2\alpha + R_y\sin^2\alpha & \frac{1}{2}(R_y - R_x)\sin 2\alpha \\ \frac{1}{2}(R_y - R_x)\sin 2\alpha & R_x\sin^2\alpha + R_y\cos^2\alpha \end{pmatrix}$$

unless $R_x=R_y$, in which case $R(\alpha)$ is independent of the rotation $\alpha$. This means that the transport between the bends must have $$N_y = M_y^{-1} M_x N_x M_x M_y^{-1} \quad (16)$$

When both the achromaticity and uncoupled conditions are satisfied the $R(\alpha)$ transfer matrix is independent of the rotation angle $\alpha$ and $R(\alpha)=R(0°)$, thus $$\sigma_{exit}(\alpha) = R(0) \cdot \sigma_{entr} \cdot R(0)^T \quad (17)$$

Mirror Symmetry

Given a beam $R=E_n \ldots E_3 E_2 E_1$, its mirror image $\check{E}=E_1 E_2 E_3 \ldots E_n$ with the order of the elements reversed can be calculated from $R^{-1}$ as $$\check{R} = S_t R^{-1} S_t \quad (18)$$

with the help of the time reversal operator $$S_t = \begin{pmatrix} \sigma_z & 0 & 0 \\ 0 & \sigma_z & 0 \\ 0 & 0 & -\sigma_z \end{pmatrix} \text{ with } \sigma_z = \begin{pmatrix} 1 & 0 \\ 0 & -1 \end{pmatrix} \quad (19)$$

where the longitudinal 2×2-block has a minus sign since the time-like coordinate z is the fifth component of the vector rather than the sixth. A palindromic beamline is formed when the second half of the particle beam contains the elements of the first half placed in reversed order. Given half the beam for $N_j$ for the $j^{th}$ 2×2 block on the diagonal as $$A = \begin{pmatrix} r & s \\ t & u \end{pmatrix} \quad (20)$$

and the mirror image for the other half, then $$N_j = \check{A} A \quad (20)$$
$$= \sigma_z A^{-1} \sigma_z A$$
$$= \begin{pmatrix} 1 & 0 \\ 0 & -1 \end{pmatrix} \begin{pmatrix} u & -s \\ -t & r \end{pmatrix} \begin{pmatrix} 1 & 0 \\ 0 & -1 \end{pmatrix} \begin{pmatrix} r & s \\ t & u \end{pmatrix}$$
$$= \begin{pmatrix} ru + st & -2su \\ 2rt & ru + st \end{pmatrix}$$

If N is build from a set of quadrupoles mirrored about the midpoint between the dipoles, then the gantry setup is guaranteed to have $N_{11}=N_{22}$ as in Eq. (14) and $N_{33}=N_{44}$ and hence $R_{11}=R_{22}$ and $R_{33}=R_{44}$.

Gantry Setup

Figure 4:
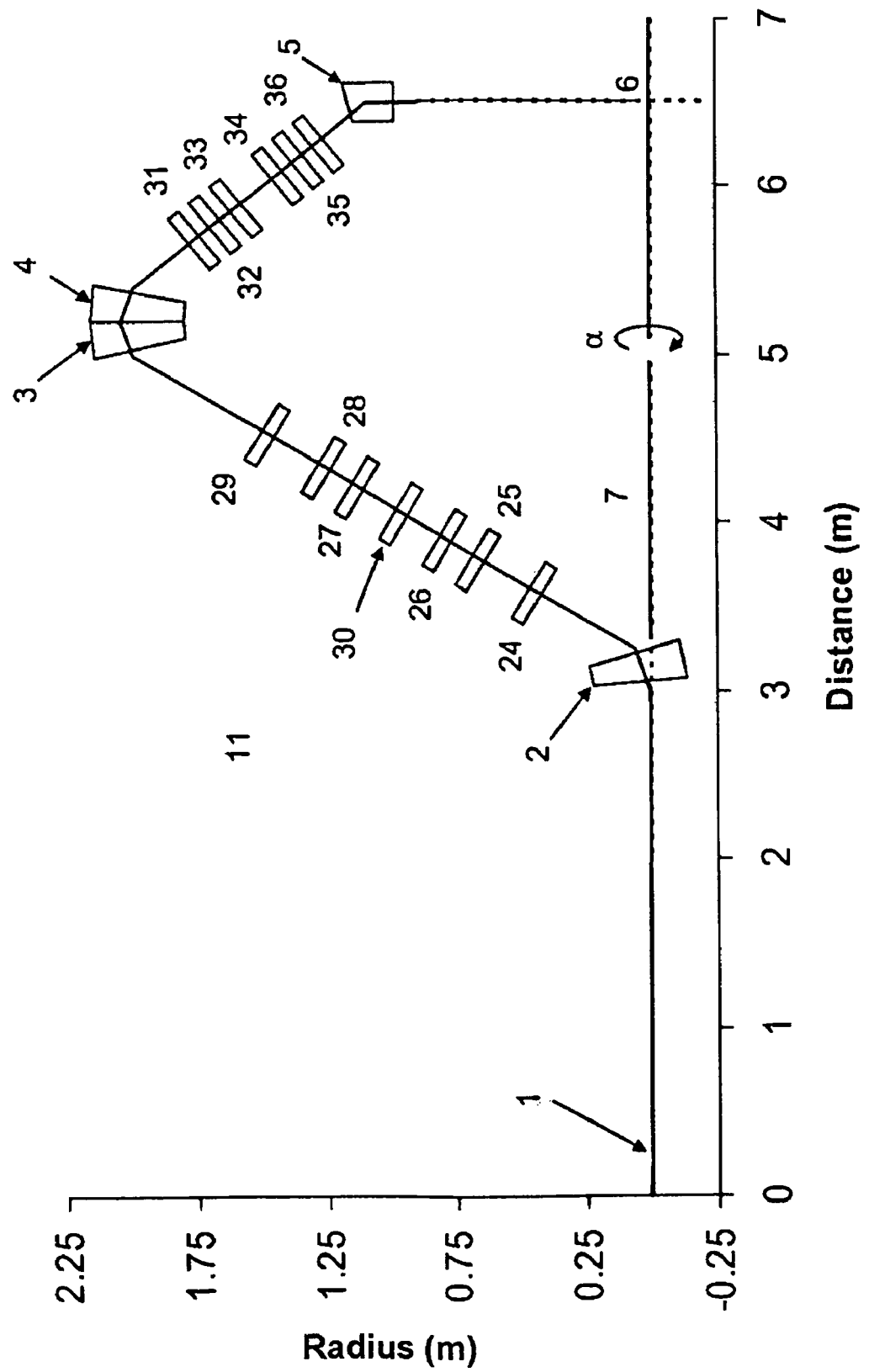
FIG. 4 is a cross-sectional view of the gantry with seven (7) quadrupole magnets between the first and second dipole magnets and six (6) quadrupole magnets between second and third dipole magnets to control beam achromaticity and coupling according to the present invention.
Figure 5:
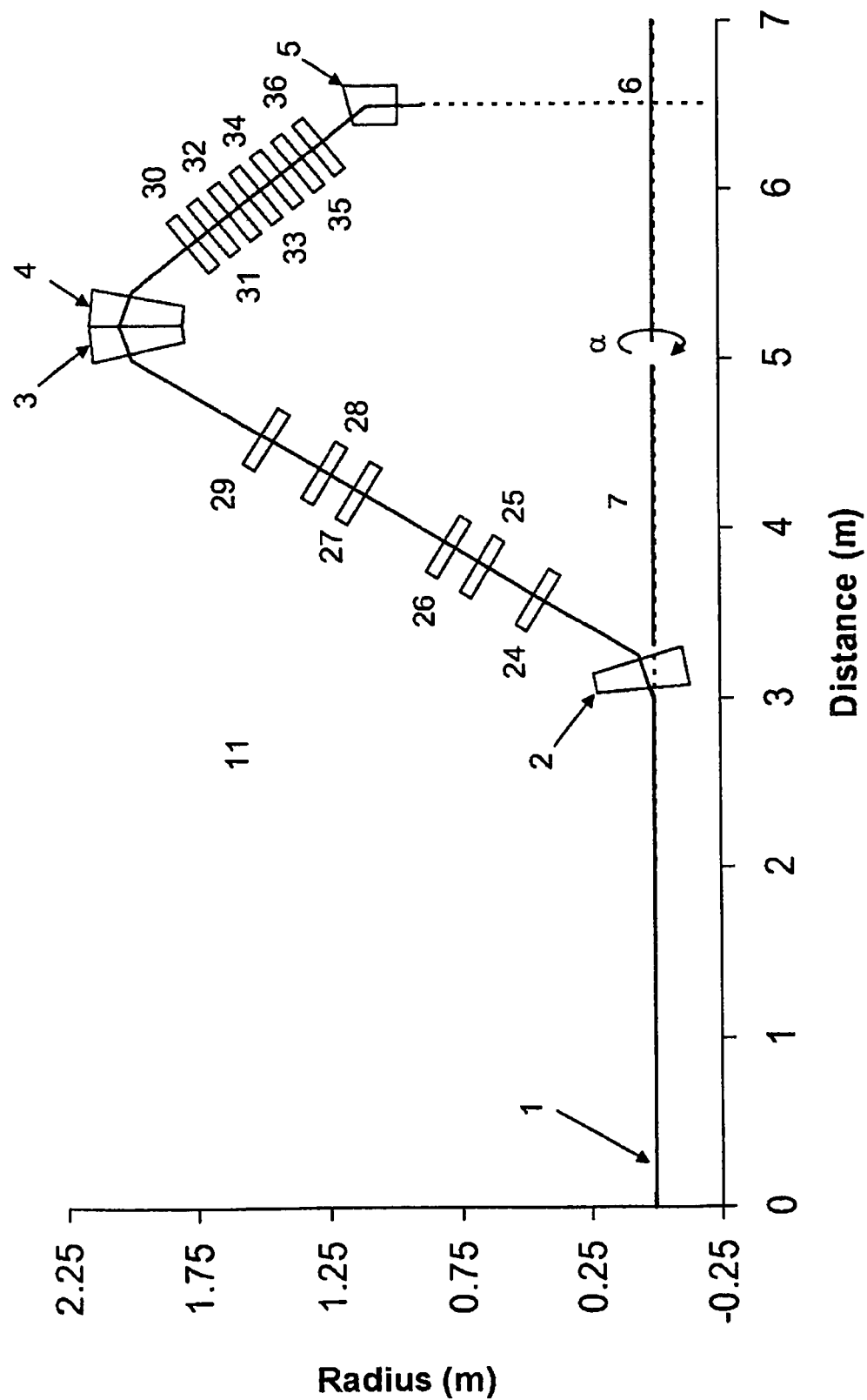
FIG. 5 is a cross-sectional view of the gantry with six (6) quadrupole magnets between the first and second dipole magnets and seven (7) quadrupole magnets between second and third dipole magnets to control beam achromaticity and coupling according to the present invention.
Figure 6:
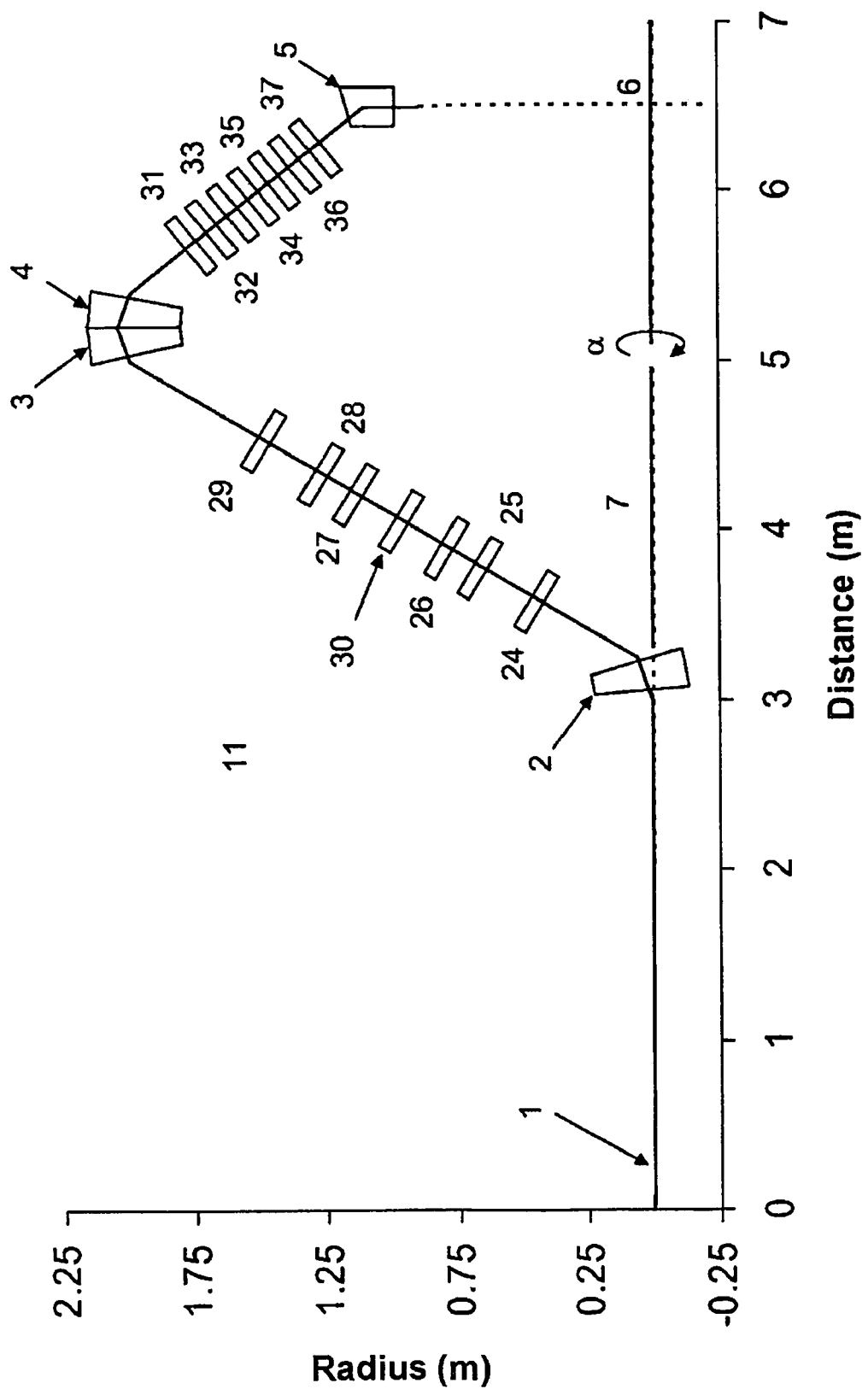
FIG. 6 is a cross-sectional view of the gantry with seven (7) quadrupole magnets between each dipole pair to control beam achromaticity and coupling according to the present invention. The quadrupole magnets are arranged in groups of seven (7) between each set of dipoles.
Figure 7:
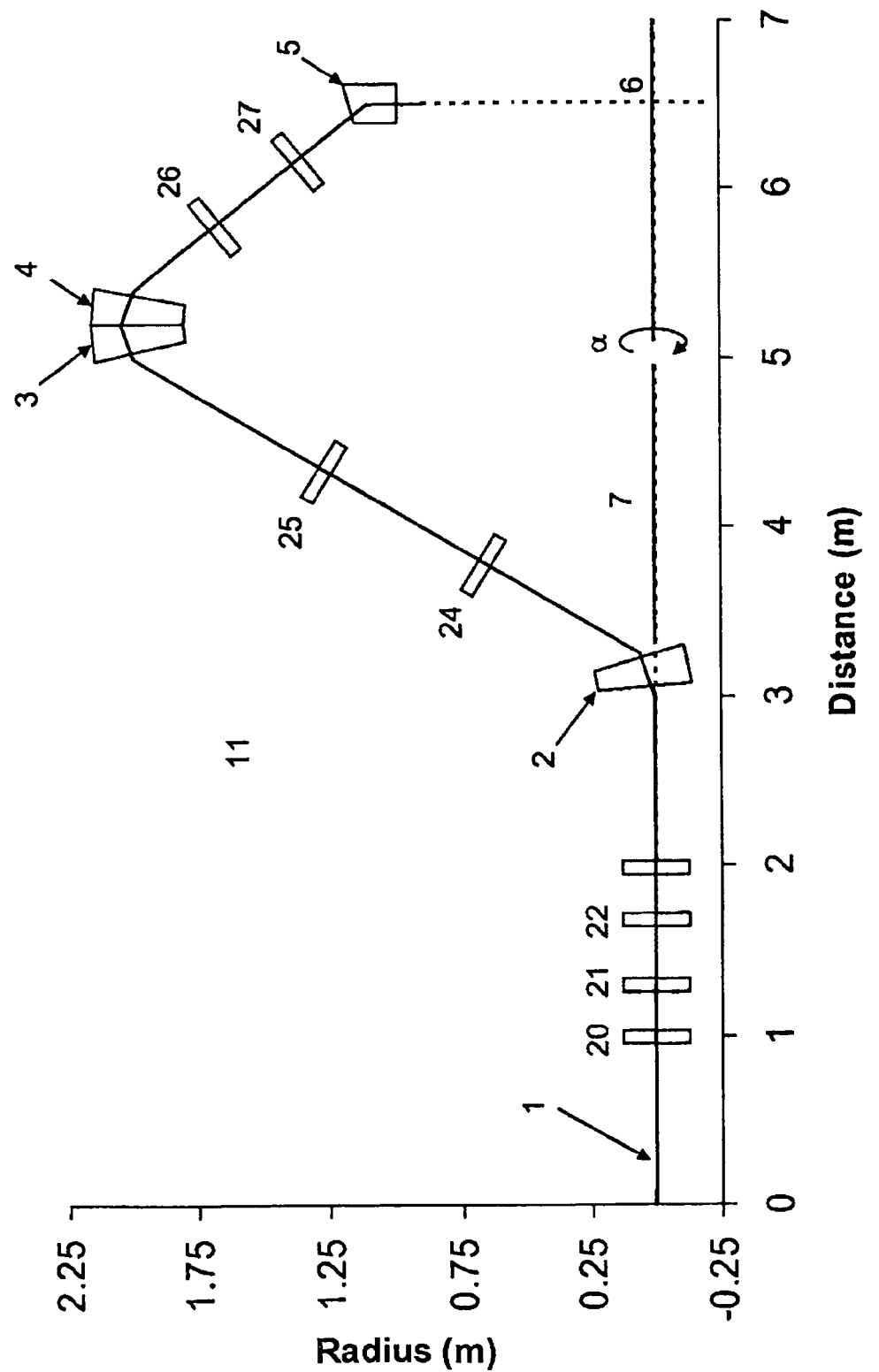
FIG. 7 is a cross-sectional view of an alternative design of a gantry that provides achromatic and uncoupled beam. The gantry is sequentially comprised of four (4) quadrupoles, placed along the rotation axis of the gantry, a dipole, two (2) quadrupoles, a dipole, two (2) quadrupoles and a dipole.

An illustrative gantry setup of the present invention is shown in FIGS. 3, 4, 5, 6, and 7. The gantry consists of two opposite sector dipoles 2 and 3 bending the beam 1 by angles $\phi$ and $\rho$ in opposite directions that provide a parallel translation of the beam in a plane 6. The gantry further includes dipole 4 and 5 that provides a redirection of the beam onto the patient/isocenter 5. Finally, the gantry consists of a plurality of quadrupoles. FIG. 3 shows a gantry setup with six quadrupoles 24-29 placed symmetrically between dipoles 2 and 3 and six quadrupoles 30-35 placed symmetrically between dipoles 4 and 5. FIG. 4 shows a gantry setup with seven quadrupoles 29-30 placed symmetrically between dipoles 2 and 3 with quadrupole 30 at the center and six quadrupoles 31-36 placed symmetrically between dipoles 4 and 5. FIG. 5 shows a gantry setup with six quadrupoles 24-29 placed symmetrically between dipoles 2 and 3 and seven quadrupoles 30-36 placed symmetrically between dipoles 4 and 5 with quadrupole 33 at the center. FIG. 6 shows a gantry setup with seven quadrupoles 24-30 placed symmetrically between dipoles 2 and 3 with quadrupole 30 at the center and seven quadrupoles 31-37 placed symmetrically between dipoles 4 and 5 with quadrupole 34 at the center. FIG. 6 shows a gantry setup with four quadrupoles 20-23 placed along the rotation axis of the gantry 6 before dipole 2, two quadrupoles 24 and 25 placed symmetrically between dipoles 2 and 3, and two quadrupoles 26 and 27 placed symmetrically between dipoles 4 and 5. The whole gantry configuration is then rotated by an angle $\alpha$ about the beam axis 6. The dipoles 3 and 4 are positioned sequentially and may be considered as two separate dipoles or as one single dipole. In one embodiment, for purposes of computer simulations, this dipoles were treated separately.

The quadrupoles were placed in pairs, e.g., 24 with 29 or 25 with 28, about the center of the line between the first and second dipole and between the second and the third dipole except for quadrupoles placed along the rotation axis before the first dipole. Each pair was excited at the same strength to achieve the desired achromatic condition described above, which also satisfies the condition $R_x=R_y$. The strength and the location of the quadrupoles is determined by the achromaticity condition ($R_{16}=0$ and $R_{26}=0$) and the mirror symmetry of the particle beam, which requires that ($R_{11}=R_{22}$) and ($R_{33}=R_{44}$). Any additional quadrupoles that have to be placed in the line to satisfy the decoupling condition $R_x=R_y$, should come in pairs to preserve the symmetry required by the achromaticity condition. Therefore the first additional pair of quadrupoles will satisfy the equality ($R_{11}=R_{33}$) and the second pair will satisfy the equality ($R_{12}=R_{34}$). The equality ($R_{21}=R_{43}$) is automatically satisfied from the symplecticity conditions ($R_{11}R_{22}=R_{12}R_{21}$) and ($R_{33}R_{44}=R_{34}R_{43}$). Thus, the minimum number of quadrupoles between two dipoles required to generate an achromatic matrix of the gantry transport line that also satisfies the condition $R_x=R_y$ is six (6), while seven (7) provide additional control on the $\beta$ functions to reduce the aperture of the following dipole in the particle beam path.

EXAMPLES

The above matrix analysis was followed by computer simulation disclosed in Examples 1-4. The gantry illustrated in FIGS. 3-7 was split into two sections. The first section incorporates dipoles 2 and 3, where dipole 2 bend the beam 1 by −20° and dipole 3 bend the beam 1 by +20°. The second section incorporates dipoles 4 and 5, where dipole 4 bends the beam 1 by +45° and dipole 5 bends the beam 11 by another 45°, thus redirecting the beam in the direction of the isocenter 6 The quadrupoles of each section were placed as exemplified below. In the computer simulations, each section was treated separately and the strength of the quadrupoles of each section was adjusted to provide an R matrix with matrix elements constrained as in Equation (8). As a result each section of the gantry is achromatic and uncoupled, therefore the R matrix of both sections combined is achromatic and uncoupled.

Example 1

The simulation of the gantry setup used two dipoles, i.e., 2 and 3, as shown in FIGS. 3 and 5, each bending the beam by 20° but in opposite directions, and 3 pairs of quadrupoles, i.e., 24-29, symmetrically placed about the center between the dipoles. For the simulation purposes, the gantry was then rotated by an angle $\alpha=22.5°$ about the beam axis. The parameters of the magnets and the drift spaces for the first half of the first section of the gantry are summarized in Table 1.

TABLE 1

Parameters of the elements for half of the six quadrupole and seven-quadrupole lines

| | Six Quadrupoles | | Seven Quadrupoles | |
|---|---|---|---|---|
| Element | ρ [m] | α | ρ [m] | α |
| DIPOLE | 0.5 | 20° | 0.5 | 20° |
| Element | L [m] | k [m$^{-2}$] | L [m] | k [m$^{-2}$] |
| DRIFT | 0.1 | — | 0.1 | — |
| QUAD | 0.15 | 36.849 | 0.15 | 29.7744 |
| DRIFT | 0.3334 | — | 0.3 | — |
| QUAD | 0.15 | −20.8498 | 0.15 | −18.8317 |
| DRIFT | 0.30106 | — | 0.724 | — |
| QUAD | 0.15 | 10.670 | 0.15 | 13.7085 |
| DRIFT | 1.1905 | — | 0.72574 | — |
| ½ QUAD | — | — | 0.075 | −27.4169 |

Figure 8:
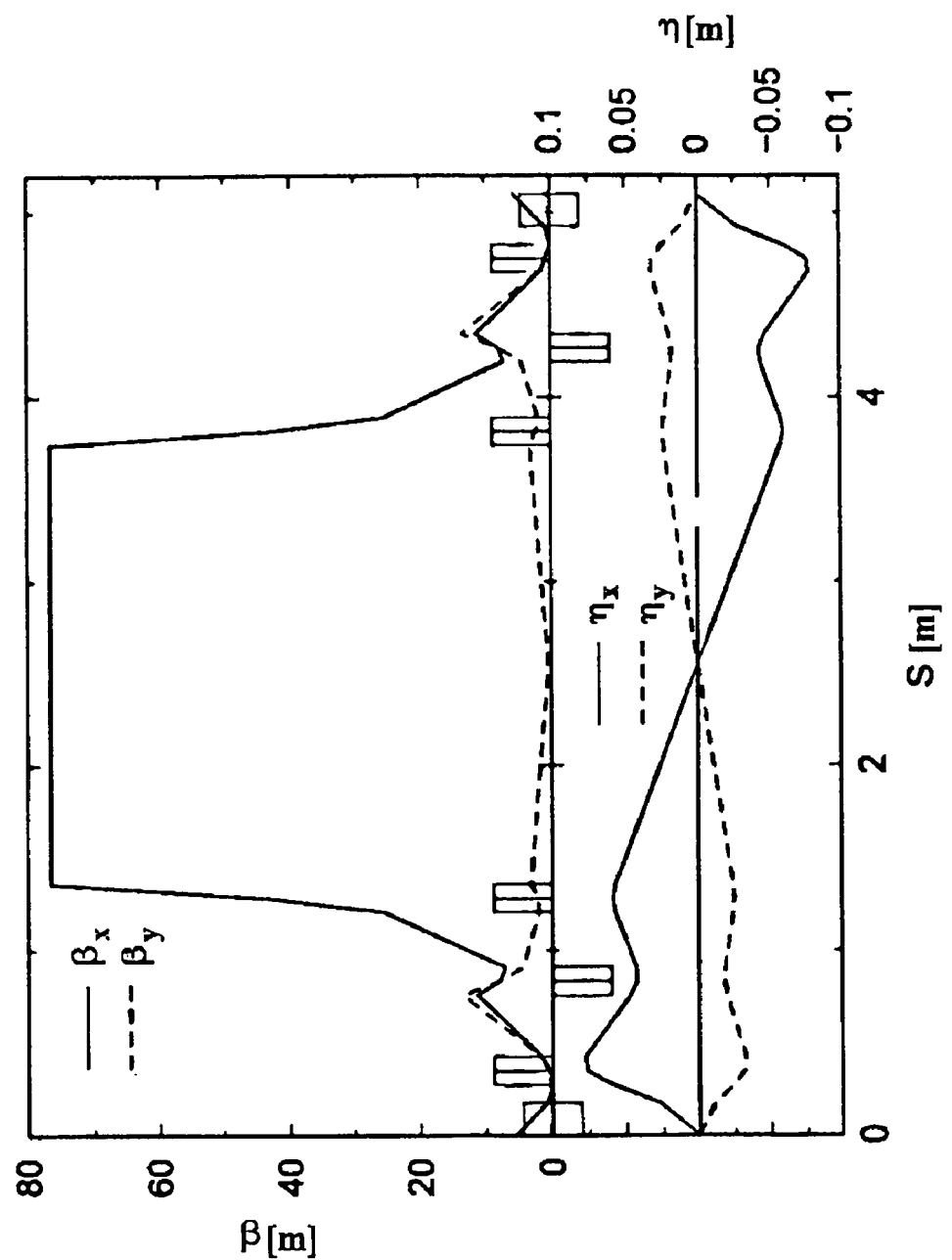
FIG. 8 shows the beta and dispersion ($\beta_x$, $\beta_y$, and $\eta_x$, $\eta_y$) functions plotted along the line as calculated using the computer code MAD in the "coupled" mode with six quadrupoles between a dipole pair as shown in FIGS. 3, 4 and 5.

FIG. 8 shows the beta functions βx, βy, and dispersion functions ηx, and ηy functions, plotted along the first section of the gantry, i.e., between dipoles 2 and 3. The values of these functions were calculated by the computer code MAD used in the "couple" mode, with the gantry rotated by an angle $\alpha=22.5°$ about the beam axis. Due to a symmetric placement of quadrupoles with respect to the center of the line, the dispersion function appears as an antisymmetric function since it transforms like the six dimensional vector x of the particle's coordinate, namely $x_{out}=Rx_{in}$. Thus $\eta_{out}=(\eta_x, \eta'_x, \eta_y, \eta'_y, 0, 1)_{out}^T = R\eta_{in}$. The symmetric placement of the quadrupoles in each section of the gantry allows also to generate a symmetric beta functions (see FIG. 8) with respect to the center of the line of each section. This is accomplished by varying the beam parameters $\alpha_x, \beta_x, \alpha_y,$ and $\beta_y$ at the entrance of the line and imposing the constrains $\alpha_x=0, \alpha_y=0$ at the center point of the line.

The matrix elements of the R matrix of the first section of the gantry satisfy the achromaticity and uncoupled conditions and are shown below.

$$\begin{pmatrix} 1.8268 & 0.2492 & 0.0000 & 0.0000 & 0.0000 & 0.0000 \\ 9.3782 & 1.8268 & 0.0000 & 0.0000 & 0.0000 & 0.0000 \\ 0.0000 & 0.0000 & 1.8268 & 0.2492 & 0.0000 & 0.0000 \\ 0.0000 & 0.0000 & 9.3782 & 1.8268 & 0.0000 & 0.0000 \\ 0.0000 & 0.0000 & 0.0000 & 0.0000 & 1.0000 & -0.0071 \\ 0.0000 & 0.0000 & 0.0000 & 0.0000 & 0.0000 & 1.0000 \end{pmatrix}$$

The elements of the R matrix of the second section of the gantry, i.e., between dipoles 4 and 5 are also constrained to satisfy the achromaticity and uncoupled conditions, therefore the R matrix of the gantry being the product of the R matrices of the two sections of the gantry, is also achromatic and uncoupled.

Example 2

Figure 9:
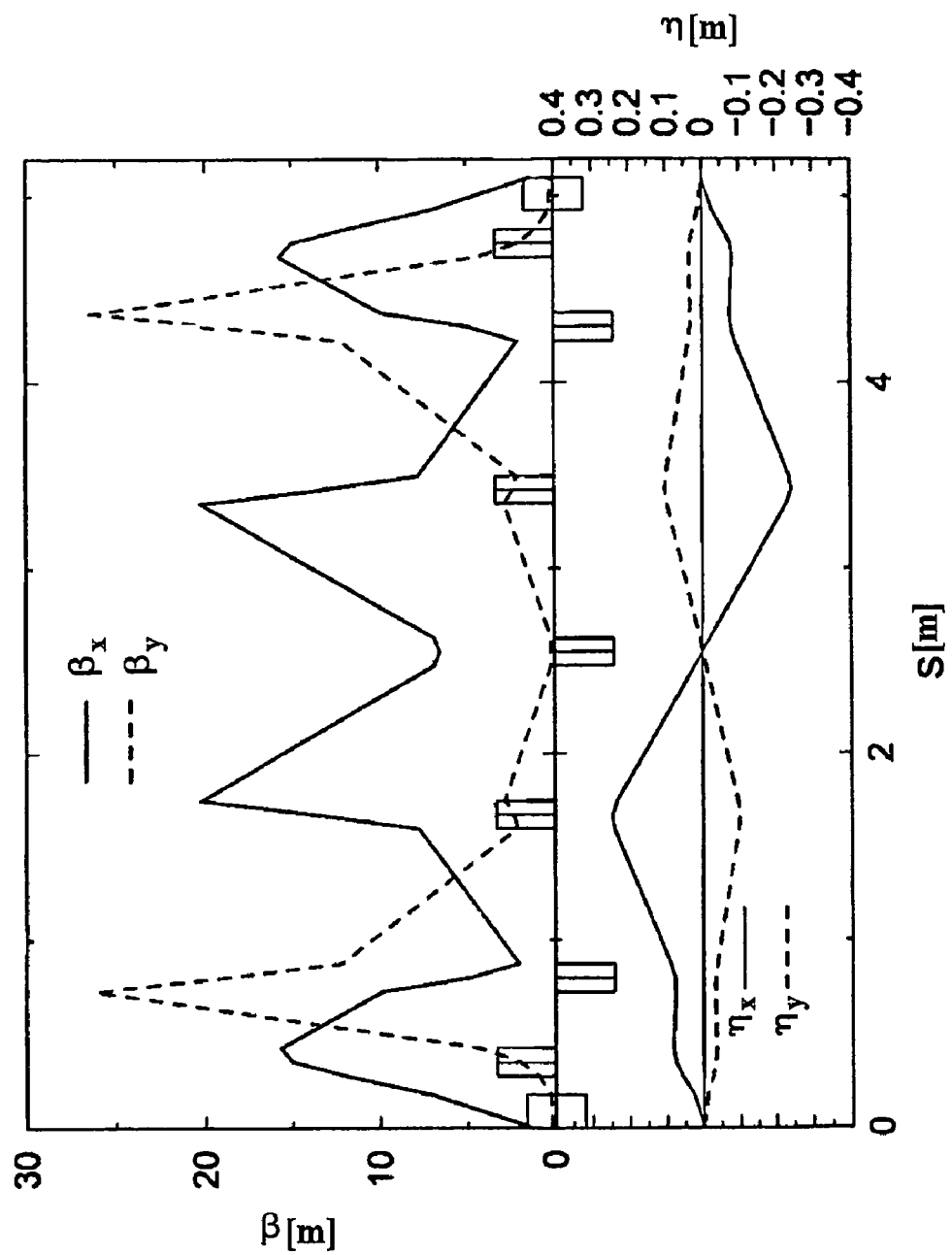
FIG. 9 shows the beta and dispersion ($\beta_x$, $\beta_y$, and $\eta_x$, $\eta_y$) functions plotted along the line as calculated using the computer code MAD in the "coupled" mode for a gantry setup with seven quadrupoles between a dipole pair as shown in FIGS. 4, 5, and 6.

In order to provide additional control on the $\beta_x, \beta_y,$ functions, an additional quadrupole, e.g., quadrupole 30 in FIGS. 4 and 6, was introduced into the setup presented in Example 1, which was placed at the center of the line to preserve the symmetry. The gantry in FIGS. 4 and 6 is also separated in two sections as in Example 1, with the difference from example 1 being that the first section, i.e., between dipoles 2 and 3, contains 7 quadrupoles. The inclusion of the 7th quadrupole (30) which was placed at the center of the line to preserve symmetry, provides additional control on the beta functions $\beta_x, \beta_y$. The parameters of the magnets and the drift spaces for the first half of the seven-quadrupoles section of the line, are summarized in Table 1. FIG. 9 shows the beta functions $\beta_x, \beta_y,$ and dispersion functions $\eta_x, \eta_y,$ plotted along the first section of the gantry. The values of these functions were calculated by the computer code MAD used in the "couple" mode, with the gantry rotated by an angle $\alpha=22.5°$ about the beam axis.

The matrix elements of the R matrix of the first section of the gantry satisfy the achromaticity and uncoupled conditions and are shown below.

$$\begin{pmatrix} 0.1882 & 0.1048 & 0.0000 & 0.0000 & 0.0000 & 0.0000 \\ -9.2079 & 0.1882 & 0.0000 & 0.0000 & 0.0000 & 0.0000 \\ 0.0000 & 0.0000 & 0.1882 & 0.1048 & 0.0000 & 0.0000 \\ 0.0000 & 0.0000 & -9.2079 & 0.1882 & 0.0000 & 0.0000 \\ 0.0000 & 0.0000 & 0.0000 & 0.0000 & 1.0000 & -0.0071 \\ 0.0000 & 0.0000 & 0.0000 & 0.0000 & 0.0000 & 1.0000 \end{pmatrix}$$

The elements of the R matrix of the second section of the gantry are also constrained to satisfy the achromaticity and uncoupled conditions, therefore the R matrix of the gantry being the product of the R matrices of the two sections of the gantry, is also achromatic and uncoupled.

Example 3

Figure 10:
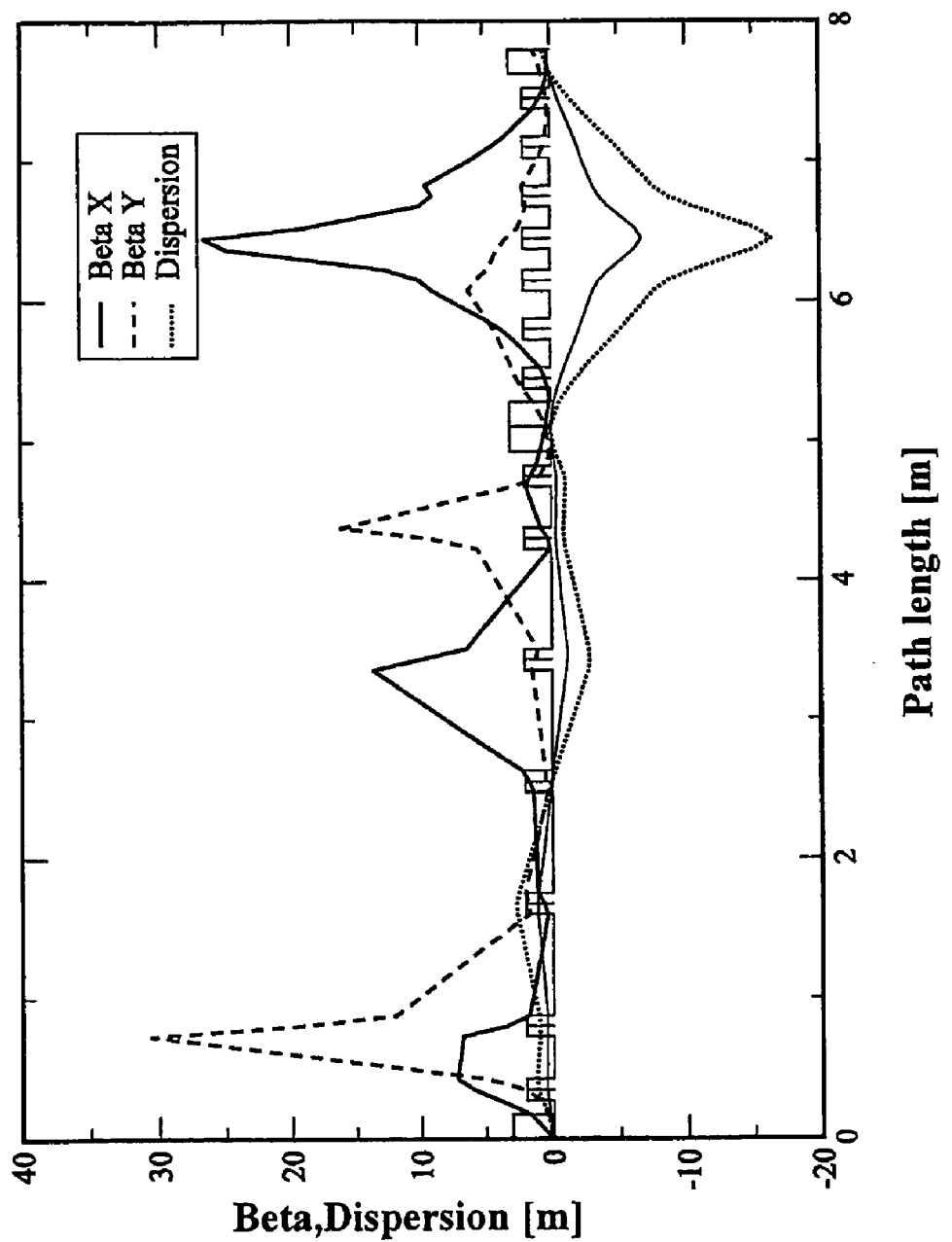
FIG. 10 shows the beta and dispersion ($\beta_x$, $\beta_y$, and $\eta_x$, $\eta_y$) functions plotted along the full gantry line as calculated using the computer code MAD in the "coupled" mode for a gantry setup with seven quadrupoles between each dipole pair as shown in FIG. 6. The values of the dispersion functions shown in the Figure are multiplied by a factor of 10.

In order to examine achromaticity and coupling control along the entire gantry, the computer simulation was ran with the setup shown in FIG. 6, however, unlike Examples 1 and 2, dipoles 3 and 4 were considered as one dipole and the gantry was not separated into two sections. FIG. 10 shows the beta functions $\beta_x$, $\beta_y$, and the dispersion functions $\eta_x$, $\eta_y$, plotted along the line as calculated using the computer code MAD in the "coupled" mode. The above discussed conditions for the rotation of the medical gantry satisfy the particle beam line to be achromatic and uncoupled over the entire gantry.

Example 4

Figure 11:
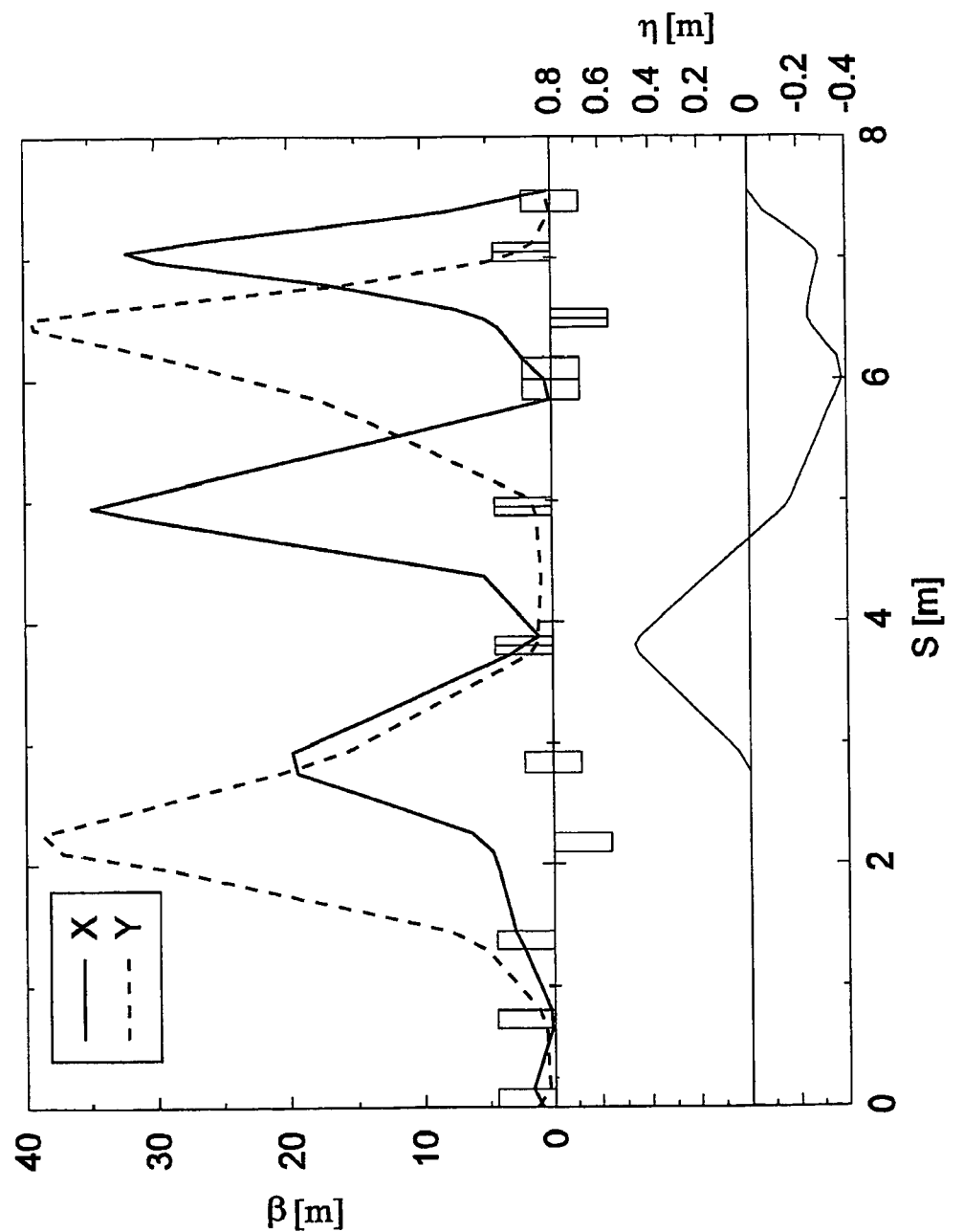
FIG. 11 shows the beta and dispersion ($\beta_x$, $\beta_y$, and $\eta_x$, $\eta_y$) functions plotted along the line as calculated using the computer code MAD in the "coupled" mode for a gantry setup with seven quadrupoles shown in FIG. 7.

In a further alternative gantry setup, the advantage of applying the achromatic and uncoupled conditions to the gantry as a whole is that it may reduce the number of quadrupoles in the gantry. In this setup, the gantry has fewer quadrupoles but still satisfies the achromatic and uncoupled conditions. The gantry is comprised of four quadrupoles 20-23 placed along the rotation axis of the gantry before the dipole 2, two quadrupoles 24 and 25 placed symmetrically between dipoles 2 and 3, and two quadrupoles 26 and 27 placed symmetrically between dipoles 4 and 5. As in Example 3, dipoles 3 and 4 were considered as one dipole and the gantry was not separated into two sections. Unlike the gantry setup presented in Examples 1-2, the achromaticity and uncoupled conditions are satisfied when all the elements of the gantry are included, whereas in Examples 1-2 the achromaticity and uncoupled conditions are satisfied within each section. FIG. 11 shows the $\beta_x$, $\beta_y$, and $\eta_x$, $\eta_y$ functions, plotted along the line as calculated using the computer code MAD in the "coupled" mode.

However, reducing the number of quadrupoles provides less control on the beta functions which determine the beam size along the line.

It will be appreciated by persons skilled in the art that the present invention is not limited to what has been particularly shown and described above. Rather, the scope of the present invention is defined by the claims which follow. It should further be understood that the above description is only representative of illustrative examples of embodiments. For the reader's convenience, the above description has focused on a representative sample of possible embodiments, a sample that teaches the principles of the present invention. Other embodiments may result from a different combination of portions of different embodiments.

The description has not attempted to exhaustively enumerate all possible variations. The alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent.

The invention claimed is:

1. A particle therapy gantry for delivering a particle beam to a patient comprising:
a beam tube defining a particle beam path;
a plurality of dipole magnets sequentially arranged along the beam tube for guiding the particle beam along the particle beam path; and
a plurality of quadrupole magnets that provide a fully achromatic and uncoupled beam transport for the unconstrained particle beam at the gantry entrance to the gantry isocenter;
wherein the size and shape of the particle beam is independent of the angle of gantry rotation, and wherein the gantry can be rotated by any angle between 0 and 360 with respect to a fixed incoming beam line
wherein the plurality of quadrupoles comprises six quadrupoles arranged in three quadrupole pairs with each quadrupole pair symmetrically arranged about the center between each pair of dipole magnets adjacent to the three quadrupole pairs.

2. A gantry as defined in claim 1, wherein a plurality of dipole magnets comprises three dipole magnets positioned sequentially from the gantry entrance that bend the particle beam along the defined particle beam path by angles that provide a translation of the beam in the direction of the isocenter.

3. A gantry as defined in claim 2, wherein each quadrupole pair is excited at the same strength to achieve the achromatic conditions and to satisfy the condition $R_x=R_y$.

4. A gantry as defined in claim 3, wherein the strength and the location of the plurality of quadrupoles is determined by the achromaticity condition $R_{16}=0$ and $R_{26}=0$, the mirror symmetry of the particle beam, which requires that $R_{11}=R_{22}$ and $R_{33}=R_{44}$, and the decoupling condition $R_x=R_y$.

5. A gantry as defined in claim 3, further comprises a quadrupole magnet placed in the center between the first and second dipole magnet to provide additional control on the .beta, functions to reduce the aperture of the second dipole magnet.

6. A gantry as defined in claim 5, wherein the strength and the location of the plurality of quadrupoles is determined by the achromaticity condition $R_{16}=0$ and $R_{26}=0$, the mirror symmetry of the particle beam, which requires that $R_{11}=R_{22}$ and $R_{33}=R_{44}$, and the decoupling condition $R_x=R_y$.

7. A gantry as defined in claim 5, wherein the strength and the location of the plurality of quadrupoles maintain the .beta, functions of less than about 30 m between the first and the second dipoles.

8. A gantry as defined in claim 7, the strength and the location of the plurality of quadrupoles maintain the .beta, functions of less than about 5.5 m at the exit of the third dipole.

9. A gantry as defined in claim 5, wherein the drift between the first and the second dipole magnet is about 5 m.

10. A gantry as defined in claim 3, further comprises a quadrupole magnet placed in the center between the second and third dipole magnet to provide additional control on the .beta, functions to reduce the aperture of the third dipole magnet.

11. A gantry as defined in claim 10, wherein the strength and the location of the plurality of quadrupoles is determined by the achromaticity condition $R_{16}=0$ and $R_{26}=0$, the mirror symmetry of the particle beam, which requires that $R_{11}=R_{22}$ and $R_{33}=R_{44}$, and the decoupling condition $R_x=R_y$.

12. A gantry as defined in claim 10, wherein the strength and the location of the plurality of quadrupoles maintain the .beta, functions of less than about 30 m between the second and the third dipoles.

13. A gantry as defined in claim 12, the strength and the location of the plurality of quadrupoles maintain the .beta, functions of less than about 5.5 m at the exit of the third dipole.

14. A gantry as defined in claim 3, further comprises a quadrupole magnet placed in the center between each pair of dipole magnets to provide additional control on the .beta, functions to reduce the aperture of the second and third dipole magnets.

15. A gantry as defined in claim 14, wherein the strength and the location of the plurality of quadrupoles is determined by the achromaticity condition $R_{16}=0$ and $R_{26}=0$, the mirror symmetry of the particle beam, which requires that $R_{11}=R_{22}$ and $R_{33}=R_{44}$, and the decoupling condition $R_x=R_y$.

16. A gantry as defined in claim 14, wherein the strength and the location of the plurality of quadrupoles maintain the .beta, functions of less than about 30 m between the second and the third dipoles.

17. A gantry as defined in claim 16, the strength and the location of the plurality of quadrupoles maintain the .beta, functions of less than about 5.5 m at the exit of the third dipole.

18. A gantry as defined in claim 2, wherein the plurality of quadrupoles comprises eight quadrupoles, wherein four quadrupoles are positioned along the axis of rotation before the first dipole magnet, two are positioned between the first and the second dipole and two are positioned between the second and the third dipole to achieve the achromatic conditions and to satisfy the condition $R_x=R_y$.

19. A gantry as defined in claim 18, wherein the strength and the location of the plurality of quadrupoles is determined by the achromaticity condition $R_{16}=0$ and $R_{26}=0$, the mirror symmetry of the particle beam, which requires that $R_{11}=R_{22}$ and $R_{33}=R_{44}$, and the decoupling condition $R_x=R_y$.

20. A method for delivering an unconstrained particle beam to a patient through a gantry comprising the steps of:
bending the unconstrained particle beam with a plurality of fixed field dipole magnets sequentially arranged along a beam tube of the gantry for the particle beam traveling in said beam tube;
maintaining the achromatic and uncoupled conditions of the particle beam from the gantry exit to the isocenter of the particle beam path by a plurality of quadrupole magnets;
wherein the size and shape of the particle beam is independent of the angle of gantry rotation for the particle beam unconstrained at the gantry entrance,
wherein the gantry can be rotated by any angle between 0 and 360 with respect to a fixed incoming beam line and wherein the plurality of quadrupoles comprises six quadrupoles arranged in three quadrupole pairs with each quadrupole pair symmetrically arranged about the center between each pair of dipole magnets adjacent to the three quadrupole pairs.

21. A method as defined in claim 20, wherein a plurality of dipole magnets comprises three dipole magnets positioned sequentially from the gantry entrance that bend the particle beam along the defined particle beam path by angles that provide a translation of the beam in the direction of the isocenter.

22. A method as defined in claim 21, wherein each quadrupole pair is excited at the same strength to achieve the achromatic conditions and the decoupling condition $R_x=R_y$.

23. A method as defined in claim 22, wherein the plurality of quadrupoles comprises six quadrupoles arranged in pairs about the center between the first and second dipole and six quadrupoles arranged in pairs about the center between the second and the third dipole.

24. A method as defined in claim 23, comprises a quadrupole magnet placed in the center between the first and the second dipole magnet to provide additional control on the .beta, functions.

25. A method as defined in claim 23, comprises a quadrupole magnet placed in the center between the second and the third dipole magnet to provide additional control on the .beta, functions.

26. A method as defined in claim 23, comprises a quadrupole magnet placed in the center between the first and the second dipole magnet and the second and the third dipole magnet to provide additional control on the .beta, functions.

27. A method as defined in claim 22, wherein the strength and the location of the plurality of quadrupoles maintain the .beta, functions of less than about 30 m between each set of dipoles and maintains the .beta, functions of less than about 5.5 m at the exit of the third dipole.

* * * * *